(12) United States Patent
Kawai et al.

(10) Patent No.: US 6,418,186 B1
(45) Date of Patent: Jul. 9, 2002

(54) X-RAY IMAGE PICKUP DEVICE

(75) Inventors: Hiroyuki Kawai, Tokyo; Ken Ueda, Ome, both of (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 09/601,219

(22) PCT Filed: Dec. 14, 1998

(86) PCT No.: PCT/JP98/05631

§ 371 (c)(1), (2), (4) Date: Jul. 28, 2000

(87) PCT Pub. No.: WO99/38439

PCT Pub. Date: Aug. 5, 1999

(30) Foreign Application Priority Data

Jan. 28, 1998 (JP) .......................................... 10-015793

(51) Int. Cl.[7] .............................................. A61B 6/03
(52) U.S. Cl. ............................. 378/19; 378/15; 378/901
(58) Field of Search ............................... 378/4, 15, 19, 378/901

(56) References Cited

U.S. PATENT DOCUMENTS 5,583,903 A * 12/1996 Saito et al. .................... 378/19
6,307,908 B1 * 10/2001 Hu ................................ 378/15
6,341,154 B1 * 1/2002 Besson .......................... 378/15
6,351,514 B1 * 2/2002 Besson .......................... 378/15

* cited by examiner

Primary Examiner—David V. Bruce
(74) Attorney, Agent, or Firm—Antonelli, Terry, Stout & Kraus, LLP (57) ABSTRACT

In an X-ray imaging apparatus in which X-ray beams are irradiated on a subject (4) and a tomogram of the subject is reconstructed from helically scanned X-ray images and displayed, reconstructing means (101) includes selecting means (105) for selecting, from X-ray images measured from the 360° periphery of the subject at a cross-sectional position specified by an inspector, X-ray images measured within a range of −360° to +360° distant from a rotation angle of an imaging system at the cross-sectional position, filter operation means (102) for applying a filtering process to the selected X-ray images, interpolation operation means (103) for interpolating projection values of X-ray images in respect of individual pixels at the cross-sectional position from distances in the moving direction of moving means (5, 6) between positions of images selected by an operation unit and the cross-sectional position specified by the inspector and the X-ray images, and inverse projection operation means (104) for reconstructing a tomogram at the cross-sectional position from an interpolated image, and the obtained tomogram is displayed on display means (9).

24 Claims, 5 Drawing Sheets

X-RAY IMAGE PICKUP DEVICE

TECHNICAL FIELD

The present invention relates to X-ray imaging apparatus (X-ray image pickup device) and more particularly, to a technology effectively applicable to multilayer detector type X-ray tomograph and method for reconstructing a tomogram of a subject from X-ray images detected by helically rotating an X-ray generating source and a multilayer X-ray detector around the subject.

BACKGROUND ART

A conventional multilayer detector type X-ray tomograph is comprised of a scan driver including an X-ray generating source and a multilayer detector, a bed including a mechanism for supporting a subject and moving it along a body-axis direction of the subject, control means for controlling the scan driver and the bed, data collection means for collecting projection data detected by the multilayer detector, reconstruction operation means for reconstructing X-ray absorption coefficient distribution of the subject from the collected projection data, display means for imaging and displaying the reconstructed X-ray absorption coefficient distribution, and a console for an operator to set values necessary for the multilayer detector type X-ray tomograph or to input commands.

DISCLOSURE OF INVENTION

Hereinafter, in the present specification hereinafter, the multilayer detector means has the meaning of a detector in which many X-ray detection elements are arranged along the rotation direction and in the rotary axis direction of the scan driver that is, in the form of a matrix which forms part of the cylindrical surface. Most X-ray tomograph put into practice at present have been so-called single-layer detector type X-ray tomograph, which has many detection elements arranged along the rotation direction on an arc. Contrarily, the multilayer detector has detectors of this type (single-layer) stacked to form layers also in the rotary axis direction and is discriminated by being called the multilayer type.

Next, a conventional imaging method by the multilayer detector type X-ray tomograph will be, described. In the multilayer detector type X-ray tomograph, too, an imaging method comparable to the method which has hitherto been known as the helical scan method is employed. More particularly, the scan driver is continuously rotated and at the same time, the bed carrying a subject is moved in the rotary axis direction; and during this operation, X-rays are projected from the X-ray generating source and X-rays transmitting through the subject are measured as projection data (X-ray images) by means of the multilayer detector. In other words, the X-ray generating source and the multilayer detector moved on orbits which are helical relative to the subject. The moving speed (moving distance per one rotation of the scan driver) of the bed and the aperture width of the detection element in the rotary axis direction (moving direction of bed) at that time were important parameters for determining spatial resolution of a reconstructed image in the rotary axis direction.

On the other hand, in the conventional single-layer detector type X-ray tomograph, the scan was carried out usually by making the moving speed of the bed nearly equal to the aperture width of the detection element in the rotary axis direction. Therefore, if the aperture width of the detection element in the rotary axis direction remains unchanged, spatial resolution nearly equal to that in usual imaging method using the single-layer detector type X-ray tomograph could be obtained with the multilayer detector type X-ray tomograph even when the moving speed of the bed approximates [the aperture width]×[the number of detector layers]. Accordingly, by forming the detector to the multilayer type, throughput could be improved.

As a reconstruction operation method of reconstructing X-ray absorption coefficient distribution in the subject, that is, a reconstructed image from projection data measured as above by the multilayer detector type X-ray tomograph, various operation methods have already been proposed and as a most fundamental multilayer detector type X-ray tomograph, an apparatus described in, for example, JP-A-4-343836 (hereinafter referred to as "literature 1") may be referred to. In the multilayer detector type X-ray tomograph described in the literature 1, projection data measured by the multilayer detector are approximately considered as projection data measured by detectors stacked up single-layer to effect reconstruction. Measurement using the multilayer detector greatly differs from that based on the single-layer detector in that projection is slanted. Namely, in the measurement using the single-layer detector, all projected X-ray beams passed through a plane containing the X-ray generating source 1 and being vertical to the rotary axis. On the other hand, in the measurement using the multilayer detector, most projections were not vertical to the rotary axis but were oblique thereto. Therefore, the more the number of layers of the detector and the larger the arrangement pitch between detector layers in the rotary axis direction, the larger the inclination becomes.

In the reconstruction operation method described in the literature 1, however, this inclination of projection was not taken into consideration. Therefore, as far as the conventional reconstruction operation method was used, actually measured X-lay beam transmitting paths differed from X-ray beam transmitting paths presupposed approximately for the reconstruction operation and as a result, there arose a problem that, for example, a partial volume artifact is generated to degrade the quality of a reconstructed image. As a method for solving the above problem, a multilayer detector type X-ray tomograph using a reconstruction operation method described in, for example, JP-A-8-322831 (hereinafter referred to as "literature 2") has been available. In the reconstruction operation method in the apparatus, the two closest X-ray beams were determined in respect of individual pixels on a reconstruction cross section and weighting complying with distances between these beams and the reconstrucntion cross section was effected to conduct subsequent inverse projection. In this manner, in the reconstruction operation method described in the literature 2, the reconstruction operation taking the inclination of projection into account was performed to thereby obtain a reconstructed image of good picture quality.

The present inventor has studied the prior arts to find the following problems. Even in the conventional multilayer detector type X-ray tomograph described in the literature 2, there arose as below. A first problem resided in the amount of operations necessary for determining the two closest X-ray beams in respect of the individual pixels on the reconstruction cross section and a second problem resided in continuity of projection.

Firstly, the first problem will be described. In utilizing the multilayer detector type X-ray tomograph, convenience will be met by the ability to suitably select the moving speed of the bed and the aperture width of the detector in the rotary axis direction depending on the condition of a subject, a region of interest in diagnosis or sought image quality or spatial resolution. Then, the combination of the two closest X-ray beams in respect of the individual pixels on the reconstruction cross section changes in various ways depending on the moving speed of the bed and the aperture width of the detector in the rotary axis direction. This combination may be calculated every operation or may be calculated in advance and held in a table. But in the former case, a problem of a drastic increase in computational amount arose. On the other hand, the latter case faced a problem of a drastic increase in table capacity.

Next, the second problem will be described. As described above, when the two closest X-ray beams were determined in respect of the individual pixels on the reconstruction cross section, there arose a problem that continuity of projection data to be inversely projected between pixels is impaired. For example, it is assumed that the two closest X-ray beams in respect of predetermined pixels are for example, an X-ray beam contained in a detector layer N1 for projection P1 and an X-ray beam contained in a detector layer N2 for projection P2. Contrarily, there is a possibility that the two closest X-ray beams in respect of pixels directly adjoining those pixels are an X-ray beam contained in a detector layer N1' (N1'≠N1) for projection P1'(P1'≠P1) and an X-ray beam contained in a detector layer N2'(N2'≠N2) for projection P2'(P2'≠P2). In other word, although the former pixels and the latter pixels are adjacent to each other, the X-ray be ms to be inversely projected belong to totally different projections. This does not seems to be of a serious problem when considering that the X-ray absorption coefficient distribution in the subject changes spatially continuously but actually, because of the presence of non-uniform sensitivity of individual detector layers and offset of incident X-rays in the rotary axis direction due to the influence of characteristics of the X-ray generating source and scattered rays, the aforementioned degradation in the continuity of X-ray beams has an influence upon image quality which is not negligible. As a result, there arose a problem that a fine streak artifact is generated on a reconstructed image to degrade the image quality of the reconstructed image.

An object of the present invention is to provide an X-ray imaging apparatus which can reconstruct a tomogram of high image quality from X-ray projection data obtained by helically scanning the periphery of a subject. Another object of the present invention is to provide an X-ray imaging apparatus capable of improving the accuracy of diagnosis by an inspector and to provide an X-ray imaging apparatus capable of reducing the amount of operations when a tomogram is reconstructed from X-ray images obtained by helically scanning the periphery of the subject. The objects and novel features of the present invention will become clear from a description of the present specification and the accompanying drawings. Typical inventions disclosed in the present application will be outlined as below.

(1) In an X-ray imaging apparatus having an X-ray generating source for irradiating X-ray beams on a subject, multilayer X-ray imaging means having two or more juxtaposed detector arrays each having X-ray detector cells 11 arranged in line and being disposed to oppose the X-ray generating source so as to measure X-ray images of the subject, rotation means for rotating an imaging system comprised of the X-ray generating source and the multilayer X-ray detecting means around the subject, moving means for relatively moving the imaging system and the subject in a body axis direction of the subject, reconstructing means for reconstructing a tomogram of the subject at a position specified by an inspector on the basis of X-ray images, and display means for displaying the tomogram, the reconstructing means comprises selecting means for selecting, from X-ray images measured from the 360° periphery of the subject at a cross-sectional position designated by the inspector, X-ray images measured within a range; of −360° to +360° distant from a rotation angle of the imaging system at the cross-sectional position, and inter polation operation means for interpolating projection values of X-ray images in respect of individual pixels at the cross-sectional position specified by the inspector from distances in the moving direction of the moving means (bed) between positions of the selected X-ray images (selected images) and the cross-sectional position specified by the inspector and the selected X-ray images, whereby the tomogram at the cross-sectional position is reconstructed from an interpolated image.

(2) In an X-ray imaging method used in the X-ray imaging apparatus as recited in (1), the step of reconstructing a tomogram of the subject executed by the reconstructing means comprises a first step of selecting, from X-ray images measured from the 360° periphery of the subject at the cross-sectional position specified by the inspector, X-ray images within a range of −360° to +360° distant from a rotation angle of the imaging system at the cross-sectional position, a second step of performing an interpolation operation for interpolating projection values of X-ray images in respect of individual pixels at the cross-sectional position by using distances in the moving direction of the moving means between positions of the selected X-ray images and the cross-sectional position and the selected X-ray images, and a third step of re constructing a tomogram at the cross-sectional position from interpolated projection values, and further, the first step includes selecting, from the X-ray images measured within the range of −360° to +360° distant from the rotation angle of the imaging system the cross-sectional position, X-ray images measure at positions where projection directions of X-ray beams are identical, (b) the first step includes selecting, from the X-ray images measured within the range of −360° to +360° distant from the rotation angle of the imaging system at the cross-sectional position, X-ray images measured at positions where projection directions of X-ray beams oppose to each other and the step of performing reconstruction has the step of correcting blur in measured X-ray images wherein the second, step includes interpolating projection values of X-ray images in respect of the individual pixels at the cross-sectional position by using corrected X-ray images, and (c) the first step includes selecting X-ray images measured by all X-ray detector cells arranged in the moving direction and the second step includes interpolating projection values of X-ray images in respect of the individual pixels at the cross-sectional position by using distances in the moving direction between the selected X-ray images and the cross-sectional position specified by the inspector and the selected X-ray images.

According to the aforementioned (1) and (2), when the interpolation operation means operates projection values in respect of the individual pixels at the cross section specified by the inspector, two sets of projection data for one rotation picked up at positions near the reconstruction cross-sectional position are selected and when projection values corresponding to pixels in respect of the individual pixels at the reconstruction cross section are calculated, projection data corresponding to predetermined X-ray beams at individual projection angles are used, the projection values can be calculated without impairing continuity of projection values to be inversely projected between pixels. Accordingly, the generation of, for example, a fine streak artifact can be prevented and as a result the image quality of the tomogram can be improved. Consequently, the efficiency of diagnosis by a doctor representing the inspector can be improved and the diagnostic accuracy can also be improved.

Further, since the projection values for the individual pixels are calculated by reflecting the distances between the X-ray beams and the reconstruction cross section, the generation of, for example, a partial volume artifact can be prevented and as a results the image quality of the tomogram can further be improved. Consequently, the efficiency of diagnosis by a doctor representing the inspector can further be improved and also, the diagnostic accuracy can further be improved. Besides, X-ray beams to be subjected to interpolation can be set easily in advance regardless of the positions of the pixels on the reconstruction cross section and hence, the amount of operations necessary for interpolation operation can be reduced. Accordingly, time required for reconstruction of a tomogram an be shortened to further improve the efficiency of diagnosis by the doctor representing the inspector.

BEST MODE FOR CARRYING OUT THE INVENTION

The present invention will be described hereunder in greater detail by making reference to embodiments of the invention and the drawings. In all figures for explaining the embodiments of the invention, components having the same function will be designated by the same reference numeral and a repetitious explanation of the components will be omitted.

Embodiment 1

Figure 1:
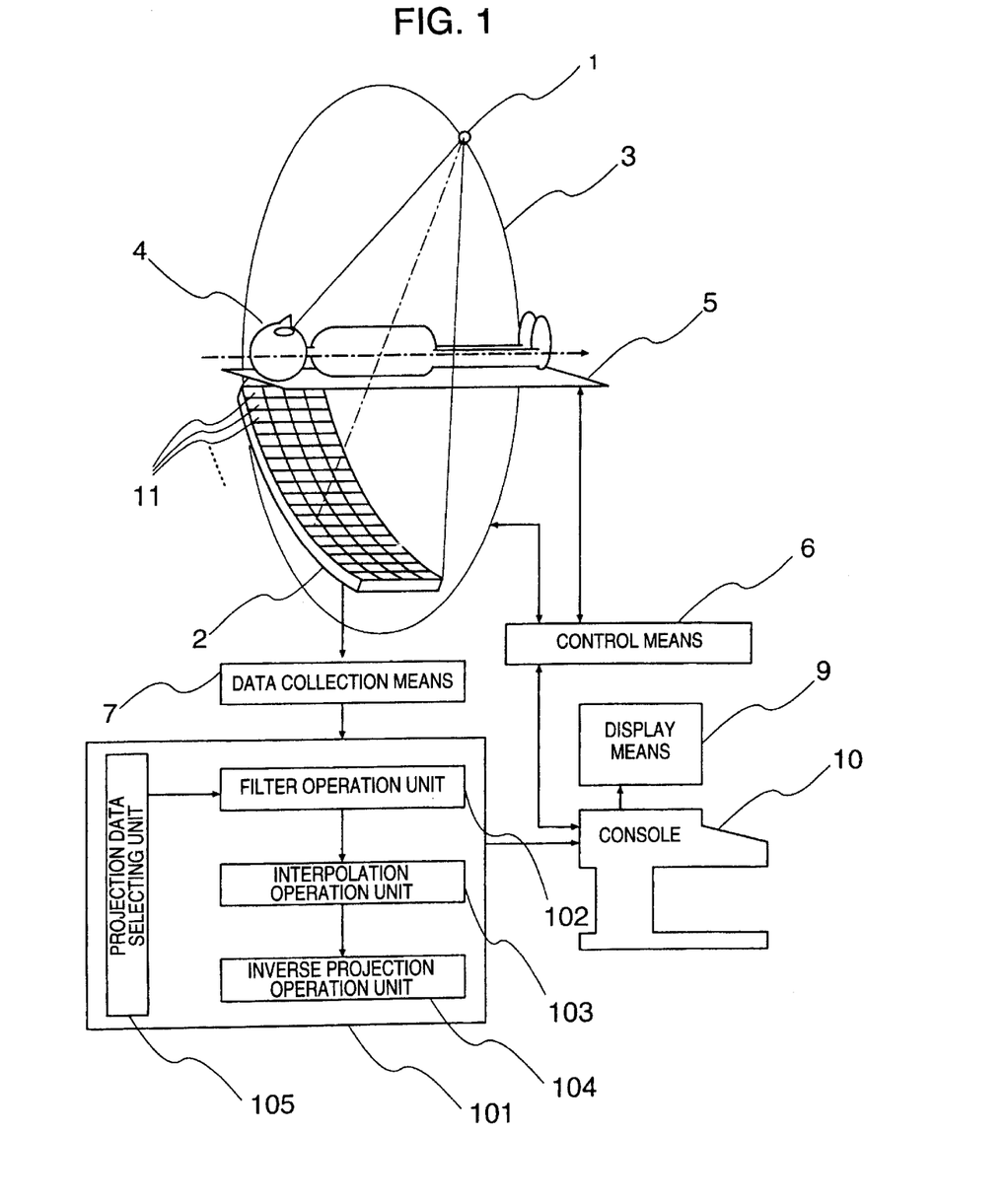
FIG. 1 is a block diagram for explaining the schematic construction of a multilayer detector type X-ray tomograph representing an X-ray imaging apparatus according to embodiment 1 of the invention.

FIG. 1 is a block diagram for explaining the schematic construction of a multilayer detector type X-ray tomograph representing an X-ray imaging apparatus according to embodiment 1 of the present invention and 1 designates an X-ray generating source, 2 designates a multilayer detector (multilayer X-ray imaging means), 3 designates a scan driver (rotation means), 4 designates a subject, 5 designates a bed, 6 designates control means, 7 designates data collection means, 9 designates display means, 10 designates a console, 101 designates reconstructing means, 102 designates a filter operation unit (filter operation means), 103 designates an interpolation operation unit (interpolation operation means), 104 designates an inverse projection operation unit (inverse projection operation means), and 105 designates a projection data selecting unit (projection data selecting means). It is to be noted that each means excepting the reconstructing means 101 has the same construction as that in the conventional multilayer detector type X-ray tomograph. Accordingly, in the present embodiment 1, the reconstructing means constructed differently from that in the conventional multilayer detector type X-ray tomograph will be described in detail.

As is clear from FIG. 1, the multilayer detector type X-ray tomograph of the present embodiment 1 is schematically constructed of the scan driver 3 having an imaging system comprised of the X-ray generating source 1 and the multilayer detector 2 of the number of detector layers being 4 and including a well-known drive mechanism adapted to support this imaging system and rotate it in a plane vertical to a body axis of the subject, the bed 5 including a tabletop for supporting (setting) the subject 4 and a well-known moving mechanism (moving means) for moving the tabletop in the body axis direction, the control means 6 implemented with, for example, a program operating on a well-known information processing apparatus constituting the console and being operative to control movement of the scan driver 3 and bed 5 on the basis of information inputted from the console 10, the data collection means 7 comprised of, for example, a well-known semiconductor memory or magnetic disk device and operative to collect and store projection data detected by the multilayer detector 2, the reconstructing means 101 implemented with, for example, a program operating on the well-known information processing apparatus and operative to reconstruct X-ray absorption coefficient distribution in the subject 4, that is, X-ray absorption coefficient distribution at a cross section specified by an inspector from the collected projection data, the console 10 constructed of, for example, the well-known information processing apparatus and an input unit thereof and operative to deliver values of measurement conditions, inputted from the input unit and required by the operator (inspector), not shown, for the multilayer detector type X-ray tomograph, to the control means 6 and reconstructing means 101 and to cause conversion means realized with a program operating on the information processing apparatus to convert the X-ray absorption coefficient distribution into image information, that is, variable density information for display so as to deliver it to the display means 9, and the display means 9 constructed of, for example, a well-known CRT (Cathode Ray Tube) unit and operative to display the image information delivered out of the console 10 on its screen.

Next, operation of the X-ray imaging apparatus of the present embodiment 1 will be described with reference to FIG. 1. When a measurement start is indicated from the console 10, the control means 6 causes, on the basis of measurement conditions inputted precedently, the X-ray generating source 1 to irradiate X-rays and controls the scan driver 3 so as to rotate the imaging system around the subject. Also, the control means 6 controls the moving mechanism, not shown, of the bed 5 so as to move the subject 4 in the body axis direction, that is, the rotary axis direction of the imaging system in synchronism with the rotation of the imaging system, so that detection (imaging) of projection data (X-ray images) at different imaging positions (phases), called helical scan, is carried out. The projection data detected by the multilayer detector 2 are collected and stored by the data collection means 7 and thereafter, they are read by the projection data selecting unit 105 of the reconstructing means 101 and delivered to the filter operation unit 102 of the reconstructing means 101. The filter operation unit 102 applies well-known filtering to the projection data delivered out of the projection data selecting unit 105 on the basis of a filter function of, for example, Shepp and Logan or Ramachandran and Lakshminarayanan and then, delivers the projection data after filtering to the interpolation operation unit 103.

In respect of the projection data after filtering, the interpolation operation unit 103 of reconstructing means 101 produces, as virtual projection data which correspond to projection data obtained when the imaging system is rotated once (rotation through 360°) while movement of the bed 5 being stopped at a position specified by the inspector (reconstruction cross-sectional position), values to be projected (hereinafter referred to as "projection values") upon individual pixels on the reconstruction cross section at individual projection angles by a well-known interpolation operation method such as polynomial interpolation of Lagrange and delivers the projection values to the inverse projection operation unit 104. Details of the interpolation operation unit 103 will be described later.

Next, the inverse projection operation unit 104 of reconstructing means 101 adds the projection values obtained during one rotation of the imaging system in respect of the individual pixels on the reconstruction cross section, that is, performs inverse projection to reconstruct X-ray absorption coefficient distribution (CT image) on the reconstruction cross section specified by the inspector. The X-ray absorption coefficient distribution is converted into variable-density information for display designated by the inspector by means of the conversion means of the console 10 and thereafter delivered to the display means 9 so as to be displayed on the display screen of the CRT unit.

Figure 2:
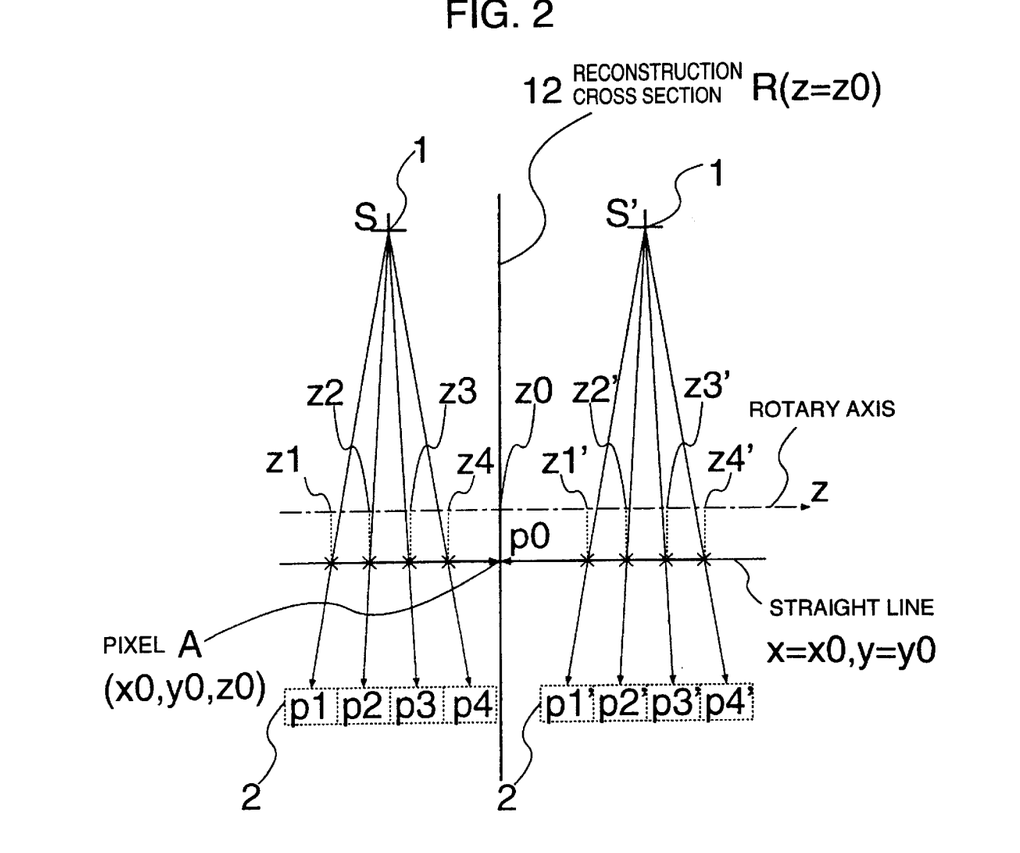
FIG. 2 is a diagram for explaining the relation between an imaging system and a reconstruction cross section specified by an inspector in the embodiment 1 of the invention.

FIG. 2 is a diagram for explaining the relation between the imaging system and the reconstruction cross section specified by the inspector. The interpolation process in the projection data selecting unit 105 and interpolation operation unit 103 in the present embodiment 1 will be described hereunder with reference to FIG. 2. It is to be noted that FIG. 2 depicts the positional relation between the imaging system and the reconstruction cross section at 360 mutually dephased positions where the projection angle is the same, that is, the positional relation between the scan driver 3 and the reconstruction cross section by using the position of the subject 4 as a criterion. Here, the rotary axis direction of the imaging system is defined as z axis, two axes set up on a cross section vertical to the rotary axis and crossing each other on the z axis are defined as x axis and y axis, an angle formed between a perpendicular drawn from X-ray generating source 1 to z axis and the x axis is defined as projection angle β, an angle formed between a straight line connecting the X-ray generating source 1 to a detector cell (detector element) constituting the multilayer detector 2 on the rotary plane of the imaging system and the perpendicular drawn from X-ray generating source 1 to z axis is defined as α, and an inclination angle from the rotary plane, that is, an inclination angle in the z axis direction is defined as γ.

In this case, as will be seen from FIG. 2, X-ray beams incident upon individual detector cells during desired projection, that is, individual pixels on the reconstruction cross section can each be expressed by using α, β and γ.

Accordingly, in the reconstructing means 101 of the present embodiment 1, the projection data selecting unit 105 first determines, as the variables α, β and γ, the projection angle of X-ray generating source 1 at the reconstruction cross-sectional position specified by the inspector from a rotation speed of the scan driver 3 and a moving speed of the bed 5. Subsequently, the projection data selecting unit 105 uses this projection angle as a criterion to select, from projection data stored in the data collecting means 7, projection data within a range of projection angle from −360° to +360° and deliver the selected projection data to the filter operation unit 102. After a well-known filter operation, the filter operation unit 102 delivers operated projection data to the interpolation operation unit 103. In respect of the individual pixels on the reconstruction cross section, the interpolation operation unit 103 interpolates projection values of corresponding pixels through an interpolation operation to be described later and then the inverse projection operation unit 104 sequentially adds (inversely projects) the projection values in respect of the corresponding pixels to reconstruct X-ray absorption coefficient distribution, that is, a tomogram. Methods for filter operation and inverse projection operation are similar to those described in the previously-described literature 2 and therefore, for details of these operations, reference may be made to the literature 2.

Figure 3:
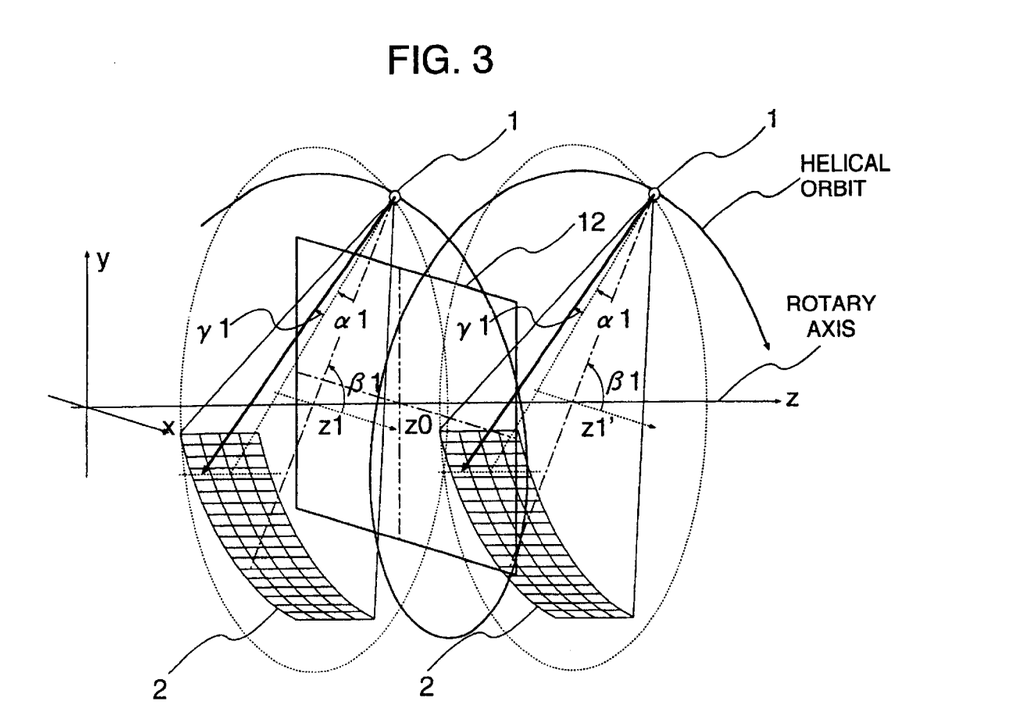
FIG. 3 is a diagram for explaining the procedure of determining projection values in respect of individual pixels on the reconstruction cross section in the embodiment 1 of the invention.

FIG. 3 is a diagram for explaining the procedure of determining projection values in respect of the individual pixels on the reconstruction cross section. Referring now to FIG. 3, the procedure for determining projection values used by the interpolation means of the present embodiment 1 for inverse projection of the individual pixels on the reconstruction cross section, that is, projection data at the reconstruction cross-sectional position will be described. In FIG. 3, for simplicity of explanation, only projection in which the projection angle is identical, that is, the X-ray generating source 1 assumes the positions S and S' and are 360° dephased from each other (for example, in the case of the projection angle shown in FIG. 2) is depicted in respect of a pixel A set on the reconstruction cross section R. On the assumption that the reconstruction cross section R is a z=z0 plane and the position of the pixel A is (x0, y0, z0) in FIG. 3, a plane passing through the positions S and S' and the position (x0, y0, z0) of the pixel A is illustrated in FIG. 3.

In the following description, an instance will be explained in which as shown in FIG. 3, individual detector elements of first to fourth layers measure projection values p1, p2, p3 and p4 during projection by the X-ray generating source 1 positioned at S and measure projection values p1', p2', p3' and p4' during projection by the X-ray generating source positioned at S' for the next phase. But it is assumed that straight line x=x0, y=y0 parallel to the z axis passing through the pixel A are sectioned by X-ray beams incident upon the detector elements at the respective projection angles at positions in z direction (on z axis) which are z1, z2, z3 and z4 and z1', z2', z3' and z4'. It will be appreciated that the positions at that time (Z1 to z4 and z1' to z4') can be calculated easily as below by using the previously-described parameters α, β and γ shown in FIG. 2.

Firstly, it is assumed that the projection angle when the X-ray generating source comes to the reconstruction cross section R (z=z0) is $\beta_0$ and the amount of movement (moving speed) in the z direction of the bed during one rotation of the scan driver is $v/(2\pi)$. Then, when the projection angle assumes $\beta_1$ or $\beta_1+2\pi$ (where $\beta_0-2\pi \leq \beta_1 < \beta_0$) the X-ray generating source S or S' assumes position $zS=z0+v(\beta_1-\beta_0)$ or $zS'=z0+v(\beta_1+2\pi-\beta_0)$. Given that the X-ray generating source-rotary axis distance is d and inclination angles of the detector elements of individual layers as viewed from the X-ray generating source are γ1 to γ4 and γ1' to γ4', Z1 to z4 and z1' to z4' can be determined pursuant to (equation 1), where n=1, 2, 3 and 4.

$$Zn=z0+v(\beta 1-\beta 0)+(d\cdot\cos\beta)\cdot\tan\gamma n/\cos(\beta 1-\alpha 1)$$

$$Zn'=Z0+V(\beta 1+2\pi-\beta 0)+(d\cdot\cos\beta 1)\cdot\tan\gamma n/\cos(\beta 1-\alpha 1) \quad \text{(equation 1)}$$

When calculating a projection value p0 to be inverse-projected on the pixel A on the reconstruction cross section R, the interpolation operation unit 103 of the embodiment 1 of the invention performs interpolation using variables of values p1 to p4 and p1' to p4' measured at the individual detector elements and relative positions z1 to z4 and z1' to z4' of the individual beams to the pixel A. The interpolation operation unit 103 in the present embodiment 1 uses polynomial interpolation of Lagrange as an interpolation function to calculate p0 as shown in (equation 2). At that time, since the interpolation operation unit 103 of the present embodiment 1 performs interpolation from 8 points, the interpolation function is of polynomial of degree seven. Accordingly, this polynomial can be operated by using, for example, an operation method of Naville to further improve the operation speed. In respect of all the pixels on the reconstruction cross section, the interpolation operation unit 103 of the present embodiment 1 applies the interpolation process based on (equation 2) to the projection data delivered out of the filter operation unit 102 and delivers the result to the inverse projection operation unit 104.

$$p0 = \frac{(z0-z2)(z0-z3)(z0-z4)(z0-z1')(z0-z2')(z0-z3')(z0-z4')p1}{(z1-z2)(z1-z3)(z1-z4)(z1-z1')(z1-z2')(z1-z3')(z1-z4')} +$$
$$\frac{(z0-z1)(z0-z3)(z0-z4)(z0-z1')(z0-z2')(z0-z3')(z0-z4')p2}{(z2-z1)(z2-z3)(z2-z4)(z2-z1')(z2-z2')(z2-z3')(z2-z4')} + \cdots +$$
$$\frac{(z0-z1)(z0-z2)(z0-z3)(z0-z4)(z0-z1')(z0-z2')(z0-z4')p3'}{(z3'-z1)(z3'-z2)(z3'-z3)(z3'-z4)(z3'-z1')(z3'-z2')(z3'-z4')} +$$
$$\frac{(z0-z1)(z0-z2)(z0-z3)(z0-z4)(z0-z1')(z0-z2')(z0-z3')p4'}{(z4'-z1)(z4'-z2)(z4'-z3)(z4'-z4)(z4'-z1')(z4'-z2')(z4'-z3')} \quad \text{(equation 2)}$$

As described above, in the X-ray imaging apparatus of the present embodiment 1, when reconstructing a tomogram at the position specified by the inspector (reconstruction cross-sectional position) from helically scanned projection data of the subject, the projection data selecting unit 105 first selects projection data at projection angles within the range of −360° to +360° distant from the reconstruction cross-sectional position. In connection with the projection data, the interpolation process is then applied to the projection data subjected to the filtering process by the filter operation unit 102. At that time, the interpolation operation unit 103 of the present embodiment 1 selects two sets of projection data for one rotation picked up at positions near the reconstruction cross-sectional position and in respect of the individual pixels on the reconstruction cross section, it first calculates positions (z1, z2, z3 and z4 and z1', z2', z3' and z4') in the rotary axis direction at which the straight line passing through the pixel and being parallel to the rotary axis is sectioned by X-ray beams incident upon the detector cells at the respective projection angles. Subsequently, the interpolation operation unit 103 calculates a projection value at the pixel of interest from the positions of the X-ray beams and the projection data (p1 to p4 and p1' to p4') in accordance with (equation 2). The interpolation operation unit 103 performs this operation for all the pixels and the projection data during one rotation to calculate projection values in respect of the individual pixels at the reconstruction cross-sectional position. The inverse projection means 104 now applies the inverse projection process to the projection values in respect of the individual pixels to reconstruct X-ray absorption coefficient distribution at the reconstruction cross-sectional position specified by the inspector.

Namely, in the multilayer detector type X-ray tomograph representing the X-ray imaging apparatus of the present embodiment 1, when reconstructing a tomogram at a reconstruction cross-sectional position specified by the inspector from helically scanned projection data, two sets of projection data measured during one rotation at positions near the reconstruction cross-sectional position are selected and projection values for inverse projection are calculated in respect of individual pixels on the reconstruction cross section. At that time, in the present embodiment 1, when calculating the projection values corresponding to the pixels, projection data corresponding to all X-ray beams at individual projection angles are used and hence, the projection values can be calculated without impairing continuity of the projection values subjected to inverse projection between the pixels. Accordingly, generation of, for example, a fine steak artifact can be prevented and as a result, the image quality of tomograms can be improved. Consequently, the efficiency of diagnosis by a doctor representing the inspector can be improved and the diagnostic accuracy can also be improved.

Besides, since the projection values are calculated in respect of the individual pixels by reflecting the distance between the X-ray beam and the reconstruction cross section, generation of a partial volume artifact can be prevented and as a result, the image quality of tomograms can further be improved. Consequently, the efficiency of diagnosis by a doctor representing the inspector can further be improved and the diagnostic accuracy can further be improved.

Further, since, in the X-ray imaging apparatus of the present embodiment 1, X-ray beams to be interpolated can be preset easily in advance regardless of the position of the pixel on the reconstruction cross section, the amount of operations necessary for the interpolation operation can be reduced. Accordingly, time required for reconstructing a tomogram can be shortened and the efficiency of diagnosis by a doctor representing the inspector can further be improved.

While, in the X-ray imaging apparatus of the present embodiment 1, the interpolation operation unit 103 calculates the projection values in respect of the individual pixels by using the Lagrange polynomial interpolation, this is not limitative and another interpolation method may be used including, for example, interpolation based on a rational function, an inter-polation operation based on a spline function or interpolation based on a curve fitted by, for example, the method of least squares, ensuring that in this case, too, the previously-described effects can obviously be attained.

Embodiment 2

Figure 4:
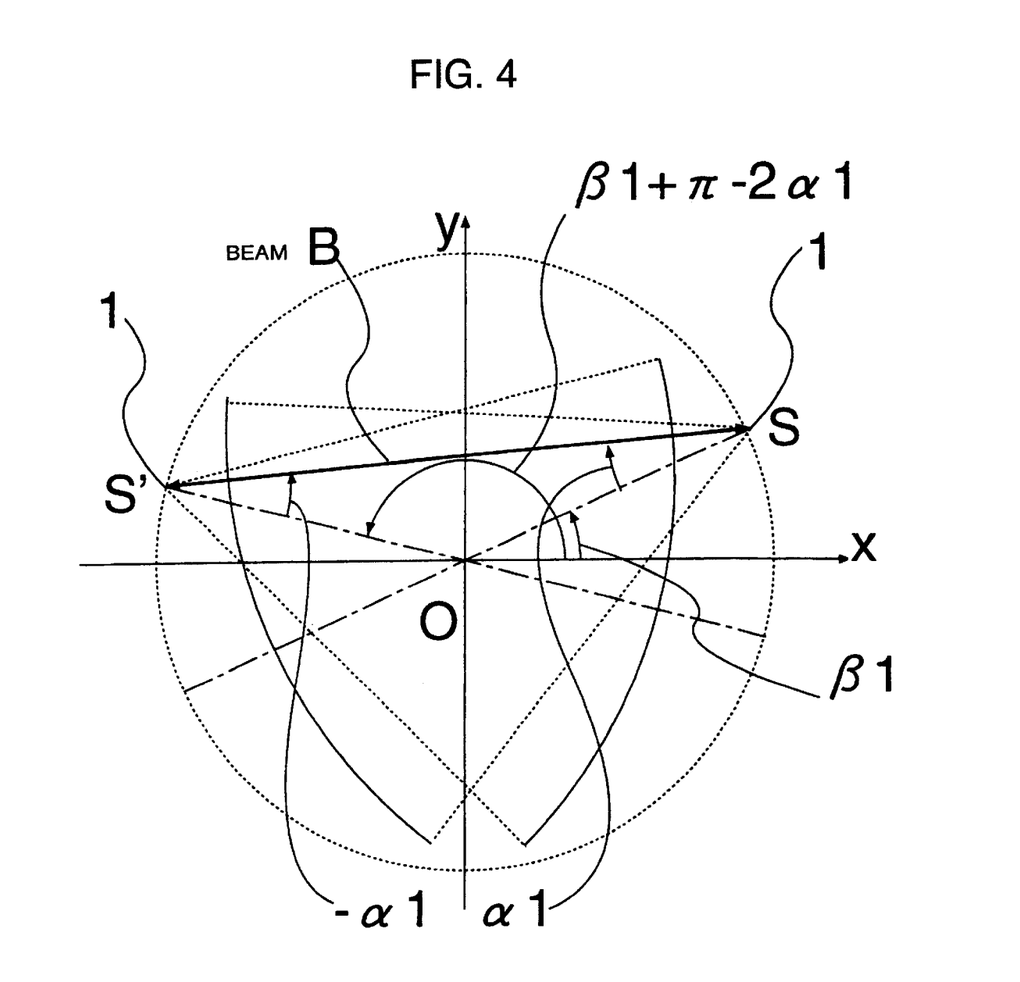
FIG. 4 is a diagram for explaining the relation between two sets of X-ray beams used for reconstruction of a tomogram in a multilayer detector type X-ray tomograph representing an X-ray imaging apparatus according to embodiment 2 of the present invention.

FIG. 4 is a diagram for explaining the relation between two sets of X-ray beams used for reconstruction of a tomogram in a multilayer detector type X-ray tomograph representing an X-ray imaging apparatus according to embodiment 2 of the present invention. In FIG. 4, however, for simplification of explanation, only the x-y plane is depicted and the scan driver 3, that is, movement in the z axis direction of the imaging system is neglected. The multilayer detector type X-ray tomograph of the present embodiment 2 differs from the multilayer detector type X-ray tomograph of the embodiment 1 only in the construction of projection data selecting unit 201 and other components are the same. Namely, the multilayer detector type X-ray tomograph of the present embodiment 2 differs from the multilayer detector type X-ray tomograph of the embodiment 1 only in that when projection values of individual pixels on a reconstruction cross section are interpolated, an interpolation operation is effected from two pieces of projection data measured near the reconstruction cross section by so called opposing beams having projection phases which are 180° dephased from each other. Accordingly, in the present embodiment 2, the projection data selecting unit 201 will be described in detail.

In FIG. 4, it is assumed that β designates a projection angle of a predetermined mating X-ray beam and α is represented by an angle α formed relative to a straight line passing through the X-ray generating source 1—rotary center (practically, inclination angle γ in the z axis direction indicating which detector layer the X-ray beam is incident upon is further needed in the multilayer detector type tomograph but it is neglected herein). In FIG. 4, an X-ray beam B during projection in which the X-ray generating source 1 is at position S is considered. This X-ray beam can be expressed in terms of (β1, α1) by using the previously-described method. Contrarily, when an X-ray beam (β1+π−2×α1, −α1) when the X-ray generating source 1 is at position S' shown in the figure is considered, it will be seen that this beam passes through the same optical path as the X-ray beam B. The X-ray beams belonging to different projections but passing through the same optical path in this manner are termed opposing beams. But, when measurement based on helical scan is carried out, the scan driver 3 moves in the z axis direction during an interval between first and second projections and therefore, the beams do not pass through the exactly identical optical path but they are also called opposing beams.

Accordingly, similarly to the interpolation operation from the 360° dephased projections shown in connection with the embodiment 1, an interpolation operation utilizing the mating opposing beams is possible. When projection values to be inversely projected are determined by the interpolation operation from the mating opposing beams, the distance in z direction between the utilized two sets of projections can be shorter than that obtained from the 360° dephased mating projections. Accordingly, as compared to the interpolation operation from the 360° dephased projections shown in the embodiment 1, a reconstructed image of higher spatial resolution can advantageously be obtained.

Figure 5:
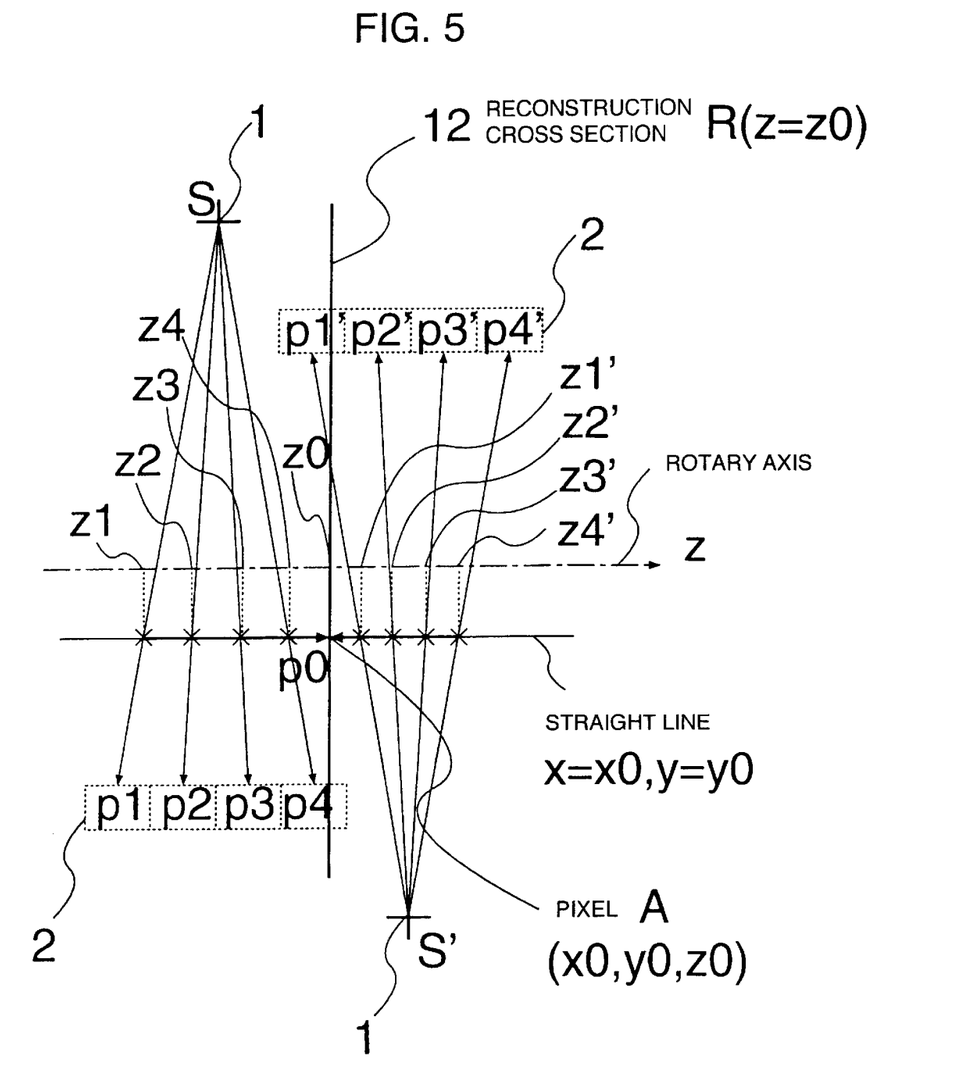
FIG. 5 is a diagram for explaining the procedure of determining projection values in respect of individual pixels on a reconstruction cross section in reconstruction means of the embodiment 2.

FIG. 5 is a diagram for explaining the procedure of determining projection values in respect of individual pixels on a reconstruction cross section in the reconstructing means of embodiment 2. Referring now to FIG. 5, the procedure for causing the projection data selecting unit of the present embodiment 2 to determine projection values used for inverse projection in respect of individual pixels on the reconstruction cross section, that is, projection data at the reconstruction cross-sectional position will be described. But in FIG. 5, too, for simplification of explanation as in the case of embodiment 1, only projections are depicted in which the projection angle is the same in relation to a pixel A set on a reconstruction cross section R, that is, the X-ray generating source 1 is at position S or S' to provide opposing beams which are 180° dephased from each other. It is assumed that when the reconstruction cross section R is a z=Z0 plane and the position of the pixel A is (x0, y0, z0), the figure shows a plane passing through S and S' and (x0, y0, z0). Presumptively, projection values p1, p2, p3 and p4 and p1', p2', p3' and p4' are measured on individual detection elements. It is also assumed that a straight line x=x0, y=y0 is sectioned by individual beams in z direction at positions z1, z2, z3 and z4 and z1', z2 , z3' and z4'.

The interpolation operation unit 103 of the present embodiment 2 now determines a projection value p0 to be inversely projected on the pixel A on the reconstruction cross section R at position z0 in z direction from the projection values p1, p2, p3 and p4 and p1', p2', p3' and p4' through an interpolation operation complying with the positions z1, z2, z3 and z4 and z1', z2', z3' and z4', that is, polynomial interpolation of Lagrange shown in equation (2). In the present embodiment 2, however, the filter process can precede the interpolation process to reduce the amount of operations necessary for the filter process, that is, to shorten the operation time and therefore, time required for reconstruction of a tomogram can be shortened. Accordingly, the efficiency of diagnosis by, for example, a doctor can be improved. Thereafter, like the embodiment 1, the inverse projection operation means 104 adds the projection values in respect of the individual pixels to determine X-ray coefficient distribution and reconstruct a tomogram at the reconstruction cross-sectional position specified by the inspector.

Comparison by Simulation

Next, for the purpose of comparing the operation time and the image quality of tomograms obtained by reconstruction in the X-ray imaging apparatus of the present embodiment 2 with those in the X-ray imaging apparatus described in the literatures 1 and 2, results of simulation conducted by a computer will be described. But, as a condition of the present simulation, a phantom having a geometrical form is virtually set and projection data obtained by irradiating X-rays on the phantom are calculated by using the computer. At that time, to enable the simulation to reflect actual imaging, necessary parameters are set as will be described below, reconstruction operations are applied to the determined projection data through the interpolation operations (interpolation methods) of the present invention and described in the literatures 1 and 2, respectively, to determine tomograms (reconstructed images) and the results are compared.

The phantom set in the present simulation is a phantom in which a plurality of small spheres each having CT value of 400 and a diameter of 0.5 mm are arranged densely in the central portion, against a cylindrical background of CT value 0 (zero) and 160 mm diameter, on a straight line 45° inclined to the z axis. Conditions of projection data generation are such that the number of detector layers is 2, the number of detector elements in one layer of the detector is 768, the number of projection operations during one rotation is 750, the aperture width of detector in the rotary axis direction is 5 mm, the moving speed of the bed 5 is 7.5 mm, the distance between the X-ray generating source 1 and the multilayer detector 2 is 1097.8 mm, the distance between the X-ray generating source 1 and the rotary center of the imaging system is 606.27 mm and the diameter of an X-ray focal point is 0.8 mm. During reconstruction, a central part of 50 mm×50 mm of the reconstruction cross section is used for a tomogram of 512×512 pixels and reconstruction is conducted through each of the reconstruction methods. In each reconstruction method, the interpolation operation using the mating opposing beams is carried out.

Finally, a profile of the part where the small spheres are arranged was determined from the tomogram and the full width at half maximum of the profile was used as a comparison criterion in the reconstruction method. Operation times consumed for reconstruction of 20 sheets of tomograms were also measured and compared. As a result, the full width at half maximum was 5.27 mm in the method described in the literature 1, 5.26 mm in the method described in the literature 2 and 4.93 mm in the method of the present invention. It was found from the results that the present invention can clearly improve the resolution of a tomogram. Given that the time required to obtain a tomogram was 1 in the method described in the literature 1, the time was 6 in the method described in the literature 2 and 4.5 in the present invention. It was found from the results that in the method of the present invention, the time required for operation is increased as compared to the method described in the literature 1 but reconstruction can be accomplished in a shorter time as compared to the method described in the literature 2.

As described above, in the multilayer detector type X-ray tomograph representing the X-ray imaging apparatus of the present embodiment 2, the interpolation operation unit 103 calculates the projection values in respect of the individual pixels on the reconstruction cross section on the basis of the projection dada related to the opposing beams selected by the projection data selecting unit 105, thereby ensuring that the projection values can be calculated without impairing continuity of the projection values to be inversely projected between pixels. Accordingly, the generation of, for example, a fine streak artifact can be prevented and as a result, the image quality of tomograms can be improved. Consequently, the efficiency of diagnosis by a doctor representing the inspector can be improved and the diagnostic accuracy can also be improved.

Besides, since the projection values are calculated in respect of the individual pixels by reflecting the distance between X-ray beam and reconstruction cross section which changes with the inclination of the X-ray beam, the generation of, for example, a partial volume artifact can be prevented and as a result, the image quality of tomograms can further be improved. Consequently, the efficiency of diagnosis by a doctor representing the inspector can further be improved and besides the diagnostic accuracy can further be improved. Further, since, in the X-ray imaging apparatus of the present embodiment 2, the X-ray beams to be subjected to interpolation can be set easily in advance regardless of the position of the pixel on the reconstruction cross section, the amount of operations necessary for interpolation operation can be reduced. Accordingly, the time required for reconstruction of a tomogram can be shortened and the efficiency of diagnosis by a doctor representing the inspector can further be improved. Further, when the projection values to be inversely projected are determined by the interpolation operation from the mating opposing beams, the distance in z direction between two sets of utilized projections can be more reduced as compared to the X-ray imaging apparatus of embodiment 1 in which the values are determined from the 360° dephased mating projections. Accordingly, a reconstructed image of further higher spatial resolution than that in the X-ray imaging apparatus of embodiment 1 can be obtained.

In the X-ray imaging apparatus of the present embodiment 2, like the X-ray imaging apparatus of the present embodiment 1, the interpolation operation unit 103 calculates the projection values in respect of the individual pixels by using the polynomial interpolation of Lagrange but this is not limitative. A different interpolation method may be used as in the case of the X-ray imaging apparatus of the present embodiment 1, including, for example, interpolation based on a rational function, interpolation operation based on a spline function or a curve fitted by the method of least squares and in this case, too, the previously-described effects can obviously be attained. While in the present embodiment the reconstruction operation using the filter correction inverse projection method has been described, this is not limitative and the present invention can obviously be applicable to the case where for example, a two-dimensional Fourier transform method or convolution method is used. In the present embodiment, the filter process is carried out in the reconstruction operation unit, the projection values are then determined in the interpolation unit and thereafter inverse projection is carried out by the reconstruction operation unit but this is not limitative. Obviously, after the projection values are determined by the interpolation unit, the filter process may be conducted by the reconstruction operation unit and thereafter the inverse projection process may be conducted.

Besides, the effects can obviously be attained similarly not only in the case of the number of detector layers being 4 but also in the case of the number of layers being either less than 4 or larger than 4. Conceivably, calculation can be simplified without using projection data detected for all the layers on the multilayer detector 2 but instead by utilizing only part of the projection data or executing a pre-process in which projection data are averaged between adjacent layers in advance and data pieces are thinned out.

Further, in the present embodiments 1 and 2, the method based on the polynomial interpolation of Lagrange indicated by (equation 2) is shown as an example of the concrete interpolation operation method in the interpolation operation unit 103. This is interpolation from 8 points and is of a polynomial of degree seven. Accordingly, this polynomial inter-polation can practically be determined in accordance with, for example, an operation method of Naville. The interpolation operation method in the interpolation operation unit 103 of the present invention is in no way limited to the polynomial interpolation method of Lagrange and as another embodiment of interpolation operation method, various operations may be conceivable including interpolation based on a rational function, an interpolation operation based on a spline function and an interpolation operation based on a curve fitted by the method of least squares. Even in these calculation methods, calculation can be conducted for all pixels on the reconstruction cross section R similarly to the method based on the previously-described polynomial interpolation of Lagrange. In any methods, X-ray beam positions z1, z2, z3 and z4 and z1', z2', z3' and z4' relative to the reconstruction cross section R differ depending on the positions of the individual pixels on the reconstruction cross section R and so, the inverse projection operation considering the inclination of projection can be effected.

While, in the multilayer detector type X-ray tomograph according to the present embodiments 1 and 2, the number of the detector layers is described as being 4 but this is not limitative. Even when the number of the detector layers is either less than or larger than 4, the present invention can of course be applied to such a case similarly to the embodiments 1 and 2. Further, calculation can be simplified without using projection data detected for all the layers on the multilayer detector 2 but instead by utilizing only part of the projection data or executing a pre-process in which projection data are averaged between adjacent layers in advance and data pieces are thinned out.

The present invention has been described concretely on the basis of the embodiments of the invention but the present invention is not limited to the embodiments of the invention set forth so far and obviously can be altered in various ways without departing from the gist of the invention.

The effects attainable by the typical inventions disclosed in the present application sill be briefed as below. (1) A tomogram of high quality can be reconstructed from X-ray images obtained by helically scanning the periphery of a subject. (2) The accuracy of diagnosis by the inspector can be improved. (3) The amount of operations necessary to reconstruct a tomogram from X-ray images obtained by helically scanning the periphery of a subject can be reduced.

In the foregoing description, reference numerals used in the drawings have the followings meanings.

1 . . . X-ray generating source, 2 . . . multilayer detector, 3 . . . scan driver, 4 . . . subject, 5 . . . bed, 6 . . . control means, 7 . . . data collection means, 9 . . . display means, 10 . . . console, 11 . . . X-ray detector cell, 12 . . . reconstructing means, 102 . . . filter operation unit, 103 . . . interpolation unit, 104 . . . inverse projection operation unit.

What is claimed is:

1. An X-ray imaging apparatus having an X-ray generating source (1) for irradiating X-ray beams on a subject, a multilayer X-ray imaging means (2) having two or more juxtaposed detector arrays each having X-ray detector cells (11) arranged in line and being disposed to oppose said X-ray generating source so as to measure X-ray images of said subject, rotation means for rotating an imaging system comprised of said X-ray generating source and said multilayer X-ray imaging means around said subject, moving means (5) for relatively moving said imaging system and said subject in a body axis direction of said subject, reconstructing means (101) for reconstructing a tomogram of said subject at a position specified by an inspector on the basis of the X-ray images, and display means (9) for displaying said tomogram, wherein said reconstructing means comprises selecting means (105) for selecting, from X-ray images measured from the 360° periphery of said subject at a cross-sectional position designated by said inspector, X-ray images measured within a range of −360° to +360° distant from a rotation angle of said imaging system at said cross-sectional position, interpolation operation means (103) for interpolating projection values of X-ray images in respect of individual pixels at said cross-sectional position by using distances in the moving direction of said moving means between positions of said selected X-ray images and said cross-sectional position and said selected X-ray images, and means (104) for reconstruction of the tomogram at said cross-sectional position from interpolated projection values.

2. An X-ray imaging apparatus according to claim 1, wherein said selecting means selects, from said X-ray images measured within a range of −360° to +360° distant from a rotation angle of said imaging system at said cross-sectional position, X-ray images measured at positions where projection directions of X-ray beams are identical.

3. An X-ray imaging apparatus according to claim 1, wherein said selecting means selects, from said X-ray images measured within a range of −360° to +360° distant from a rotation angle of said imaging system at said cross-sectional position, X-ray images measured at positions where projection directions of X-ray beams oppose to each other.

4. An X-ray imaging apparatus according to claim 3, wherein said reconstructing means comprises correction means (102) for correcting blur in measured X-ray images, and said interpolation operation means interpolates projection values of X-ray images in respect of the individual pixels at said cross-sectional position by using said corrected X-ray images.

5. An X-ray imaging apparatus according to claim 1, wherein said selecting means selects X-ray images measured by all of said X-ray detector cells arranged in the moving direction, and said interpolation operation means interpolates projection values of X-ray images in respect of the individual pixels at said cross-sectional position by using distances in said moving direction between the selected X-ray images and said cross-sectional position and said selected X-ray images.

6. An X-ray imaging apparatus according to claim 2, wherein said selecting means selects X-ray images measured by all of said X-ray detector cells arranged in the moving direction, and said interpolation operation means interpolates projection values of X-ray images in respect of the individual pixels at said cross-sectional position by using distances in said moving direction between the selected X-ray images and said cross-sectional position and said selected X-ray images.

7. An X-ray imaging apparatus according to claim 3, wherein said selecting means selects X-ray images measured by all of said X-ray detector cells arranged in the moving direction, and said interpolation operation means interpolates projection values of X-ray images in respect of the individual pixels at said cross-sectional position by using distances in said moving direction between the selected X-ray images and said cross-sectional position and said selected X-ray images.

8. An X-ray imaging apparatus according to claim 4, wherein said selecting means selects X-ray images measured by all of said X-ray detector cells arranged in the moving direction, and said interpolation operation means interpolates projection values of X-ray images in respect of the individual pixels at said cross-sectional position by using distances in said moving direction between the selected X-ray images and said cross-sectional position and said selected X-ray images.

9. An X-ray imaging method used in an X-ray apparatus having an X-ray generating source (1) for irradiating X-ray beams on a subject, multilayer X-ray imaging means (2) having two or more juxtaposed detector arrays each having X-ray detector cells (11) arranged in line and being disposed to oppose said X-ray generating source so as to measure X-ray images of said object, rotation means for rotating an imaging system comprised of said X-ray generating source and said multilayer X-ray imaging means around said subject, moving means (5) for relatively moving said imaging system and said subject in a body axis direction of said subject, reconstructing means (101) for executing a step of performing reconstruction of a tomogram of said subject at a position specified by an inspector on the basis of the X-ray images, and display means (9) for displaying said tomogram, wherein said step of performing reconstruction comprises a first step of selecting, from X-ray images measured from the 360° periphery of said subject at the cross-sectional position specified by said inspector, X-ray images within a range of −360° to +360° distant from a rotating angle of said imaging system at said cross-sectional position, a second step of performing an interpolation operation for interpolating projection values of X-ray images in respect of individual pixels at said cross-sectional position by using distances in the moving direction of said moving means between positions of the selected X-ray images and said cross-sectional position and said selected X-ray images, and a third step of reconstructing a tomogram at said cross-sectional position from interpolated projection values.

10. An X-ray imaging method according to claim 9, wherein said first step includes selecting, from the X-ray images measured within the range of −360° to +360° distant from the rotation angle of said imaging system at said cross-sectional position, X-ray images measured at positions where projection directions of X-ray beams are identical.

11. An X-ray imaging method according to claim 9, wherein said first step includes selecting, from the X-ray images measured within the range of −360° to +360° distant from the rotation angle of said imaging system at said cross-sectional position, X-ray images measured at positions where projection directions of X-ray beams oppose to each other.

12. An X-ray imaging method according to claim 11, wherein said step of performing reconstruction has a step of correcting blur in measured X-ray images and said second step includes interpolating projection values of X-ray images in respect of the individual pixels at said cross-sectional position by using corrected X-ray images.

13. An X-ray imaging method according to claim 9, wherein said first step includes selecting X-ray images measured by all of the X-ray detector cells arranged in the moving direction and said second step includes interpolating projection values of X-ray images in respect of the individual pixels at said cross sectional position by using distances between the selected X-ray images and said cross-sectional position and said selected X-ray images.

14. An X-ray imaging method according to claim 10, wherein said first step includes selecting X-ray images measured by all of the X-ray detector cells arranged in the moving direction and said second step includes interpolating projection values of X-ray images in respect of the individual pixels at said cross-sectional position by using distances between the selected X-ray images and said cross-sectional position and said selected X-ray images.

15. An X-ray imaging method according to claim 11, wherein said first step includes selecting X-ray images measured by all of the X-ray detector cells arranged in the moving direction and said second step includes interpolating projection values of X-ray images in respect of the individual pixels at said cross-sectional position by using distances between the select ed X-ray images and said cross-sectional position and said selected X-ray images.

16. An X-ray imaging method according to claim 12, wherein said first step includes selecting X-ray images measured by all of the X-ray detector cells arranged in the moving direction and said second step includes interpolating projection values of X-ray images in respect of the individual pixels at said cross-sectional position by using distances between the selected X-ray images and said cross-sectional position and said X-ray images.

17. An X-ray imaging apparatus having an X-ray generating source (1) for irradiating X-rays on a subject, multi-layer X-ray imaging means (2) having two or more juxtaposed detector arrays each having X-ray detector cells (11) arranged in line and being disposed to oppose said X-ray generating source so as to detect projection data of said subject, rotation means for rotating an imaging system comprised of said X-ray generating source and said multi-layer X-ray detecting means around said subject, moving means (5) for moving said subject in a direction of body axis of said subject, reconstructing means (101) for reconstructing a tomogram of said subject at a cross section specified by an inspector, and display means (9) for displaying said tomogram, said reconstructing means comprising selecting means (105) for selecting projection data at projection angles within a range of −360° to +360° distant from said cross section, interpolation operation means (103) being operative to select two sets of said projection data for one rotation which are detected at positions near said cross section, to determine positions of intersections in the rotary axis direction where a straight line passing through one of pixels on said cross section and being parallel with said rotary axis of said rotation means intersects X-ray beams incident upon the individual X-ray detector cells at the individual projection angles and to perform, in respect of projection data obtained with all pixels on said cross section during said one rotation, an operation necessary to determine projection data at said one pixel through interpolation by using the positions in said rotary axis direction of said intersections and said projection data corresponding to all the X-ray beams at the individual projection angles so as to determine projection data in respect of the individual pixels at said cross section through said interpolation, and means (104) for reconstructing said tomogram at the position of said cross section from the projection data obtained by said interpolation operation means.

18. An X-ray imaging apparatus according to claim 17, wherein said selecting means selects projection data which are at the same projection angles and which are 360° dephased from each other.

19. An X-ray imaging apparatus according to claim 17, wherein said selecting means selects projection data which are 180° dephased from each other.

20. An X-ray imaging apparatus according to claim 19, wherein said reconstructing means includes filter operation means (102) for performing a filter operation of said projection data selected by said selecting means, and said projection data after said filter operation are delivered to said inter-polation operation means.

21. An X-ray imaging apparatus according to claim 17, wherein said selecting means selects projection data detected by all of said X-ray detector cells arranged in the moving direction of said moving means.

22. An X-ray imaging apparatus according to claim 18, wherein said selecting means selects projection data detected by all of said X-ray detector cells arranged in the moving direction of said moving means.

23. An X-ray imaging apparatus according to claim 19, wherein said selecting means selects projection data selected by all of said X-ray detector cells arranged in the moving direction of said moving means.

24. An X-ray imaging apparatus according to claim 20, wherein said selecting means selects projection data selected by all of said X-ray detector cells arranged in the moving direction of said moving means.

* * * * *